(12) United States Patent
Eng et al.

(10) Patent No.: US 7,971,276 B2
(45) Date of Patent: Jul. 5, 2011

(54) GLOVE WITH HAND-FRIENDLY COATING AND METHOD OF MAKING

(75) Inventors: Aik Hwee Eng, Petaling Jaya (MY); Hee Meng Lai, Melaka (MY); Bit New Yee, Kuantan (MY); Soo Hwa Kwan, Melaka (MY); Dave Narasimhan, Flemington, NJ (US)

(73) Assignee: Ansell Healthcare Products, LLC, Red Bank, NJ (US)

( * ) Notice: Subject to any disclaimer, the term of this patent is extended or adjusted under 35 U.S.C. 154(b) by 544 days.

(21) Appl. No.: 11/291,227

(22) Filed: Dec. 1, 2005

(65) Prior Publication Data

US 2006/0070167 A1 Apr. 6, 2006

(51) Int. Cl.
*A41D 19/00* (2006.01)

(52) U.S. Cl. .......... 2/161.7; 2/159; 2/167; 2/168; 2/901; 424/401; 424/776; 428/35.7; 524/415

(58) Field of Classification Search .................. 428/35.7; 2/167, 159, 161.7, 168, 901; 424/401, 776; 524/415

See application file for complete search history.

(56) References Cited

U.S. PATENT DOCUMENTS

| | | | |
|---|---|---|---|
| 3,896,807 A * | 7/1975 | Buchalter | 604/289 |
| 4,095,293 A | 6/1978 | Heavner et al. | |
| 5,614,202 A | 3/1997 | DeFina | |
| 5,985,955 A * | 11/1999 | Bechara et al. | 523/415 |
| 6,075,081 A | 6/2000 | Nile et al. | |
| 6,274,154 B1 | 8/2001 | Chou et al. | |
| 6,294,186 B1 * | 9/2001 | Beerse et al. | 424/405 |
| 6,347,409 B1 | 2/2002 | Nile et al. | |
| 6,352,666 B1 | 3/2002 | Nile et al. | |
| 6,423,328 B2 | 7/2002 | Chou et al. | |
| 6,468,551 B1 * | 10/2002 | Diec et al. | 424/401 |
| 6,630,152 B2 | 10/2003 | Chou et al. | |
| 6,638,587 B1 | 10/2003 | Wang et al. | |
| 6,692,756 B2 | 2/2004 | Chou et al. | |
| 6,709,725 B1 | 3/2004 | Lai et al. | |
| 6,772,443 B2 | 8/2004 | Soerens et al. | |
| 6,787,490 B2 | 9/2004 | Shipp, Jr. | |
| 6,939,617 B2 | 9/2005 | Koide et al. | |
| 6,953,582 B2 | 10/2005 | Chou et al. | |
| 2001/0053421 A1 | 12/2001 | Schaller | |

(Continued)

FOREIGN PATENT DOCUMENTS

JP 2004/190164 7/2004

(Continued)

OTHER PUBLICATIONS

PCT/US05/46014, "PCT International Search Report", Oct. 17, 2007.

(Continued)

*Primary Examiner* — Brent T O'Hern
(74) *Attorney, Agent, or Firm* — Moser IP Law Group

(57) ABSTRACT

A hand-friendly rubber glove article comprising a dried coating of an emulsified hand-friendly mixture comprising at least one water-soluble humectant moisturizer, at least one water-soluble lubricant, at least one water-soluble surfactant, and at least one water-insoluble occlusive moisturizer, which is finely and substantially uniformly dispersed within the mixture, which is transferred to the skin of a wearer upon activation with skin-generated moisture, and, optionally, a fabric-adherent cuff region and/or a texturized surface and methods of making the emulsified hand-friendly mixture and the glove article.

20 Claims, 1 Drawing Sheet

U.S. PATENT DOCUMENTS

| | | |
|---|---|---|
| 2004/0115250 A1 | 6/2004 | Loo et al. |
| 2004/0115379 A1 | 6/2004 | Conley et al. |
| 2004/0122382 A1* | 6/2004 | Johnson et al. ............... 604/292 |
| 2004/0126604 A1 | 7/2004 | Wang et al. |
| 2004/0217506 A1* | 11/2004 | Vistins .......................... 264/129 |
| 2004/0241201 A1 | 12/2004 | Wang et al. |
| 2004/0255362 A1* | 12/2004 | Soerens et al. ................. 2/161.7 |
| 2005/0081278 A1* | 4/2005 | Williams .......................... 2/167 |
| 2005/0100621 A1 | 5/2005 | Popp et al. |
| 2005/0186258 A1* | 8/2005 | Wang et al. .................... 424/443 |
| 2005/0222543 A1 | 10/2005 | Shao |
| 2006/0059604 A1 | 3/2006 | Lai et al. |
| 2006/0062815 A1 | 3/2006 | Djie |
| 2008/0020023 A1 | 1/2008 | Wang et al. |

FOREIGN PATENT DOCUMENTS

| | | |
|---|---|---|
| WO | WO 2004/037305 A1 | 5/2004 |
| WO | WO 2004/060338 A1 | 7/2004 |
| WO | WO 2004/060432 A1 | 7/2004 |
| WO | WO 2004/098431 A1 | 11/2004 |
| WO | WO 2005/036996 A2 | 4/2005 |

OTHER PUBLICATIONS

PCT/US05/46014, "PCT Written Opinion", Oct. 17, 2007.

Extended EPO Search Report in EP 05 85 4683, corresponding to PCT/US2005/046014, (Mar. 30, 2009), 7 pp.

* cited by examiner

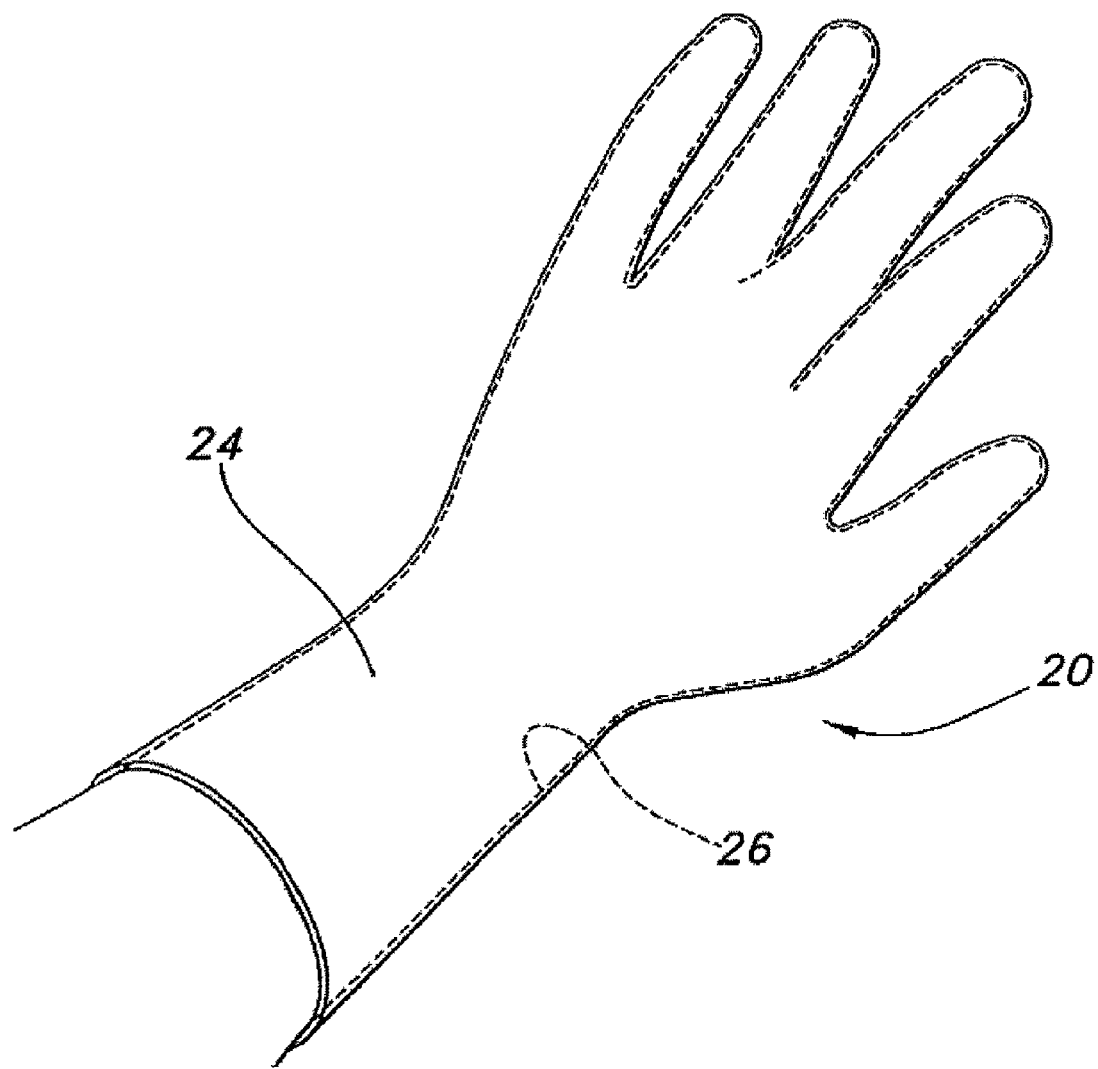
Fig.

GLOVE WITH HAND-FRIENDLY COATING AND METHOD OF MAKING

TECHNICAL FILED OF THE INVENTION

The present invention relates to rubber glove articles with a hand-friendly coating on the skin-contacting surface and a method of making same.

BACKGROUND OF THE INVENTION

Skin-contacting articles, such as gloves, particularly medical gloves, are commonly used as a protective barrier against the contamination of the user by chemicals and body fluids containing micro-organisms including bacteria and/or viruses and the like. In addition, the gloves also protect the user from injuries that result from abrasive action. As such, these gloves and other skin-contacting articles are manufactured in such a way that they are entirely impermeable to the contaminants or microorganisms during use. To maintain this barrier integrity, gloves need to be free from defects, such as holes (e.g., pinholes) and tears.

The gloves also must have easy donning and doffing properties, particularly for medical glove applications, where the time available for glove donning can be a matter of seconds. There are three specific aspects of donning properties related to medical gloves, more specifically surgical gloves, namely dry hand donning, damp-hand or wet-hand donning, and double gloving. If the user encounters difficulty in donning a glove, normally the user will give up donning of the particular glove and try to select a glove that provides superior donning properties. Surgical glove users normally wash their hands before donning the gloves. In most cases, their hands are either damp or wet when donning the gloves is attempted. In many cases, gloves are double donned, one glove on top of the other, in order to provide an additional glove barrier layer. If the outer glove tears or is cut, the surgeon can simply remove the outer glove without having to wash hands and start the glove donning process all over again, a task which takes additional time during surgery. Therefore, the double donning or double gloving properties are extremely important. To achieve good double gloving properties, the inside surface of the outer glove and the outside surface of the inner glove need to be smooth so that they can easily slide against each other. However, the outside surface of the glove should not be too smooth, as this would result in poor grip properties, causing difficulty to the user in holding or handling surgical instruments. Therefore, the outside surface of the gloves should have a certain level of tack for providing good grip properties and yet not cause difficulty in double gloving to the user, while the inside surface of the gloves should be as smooth as possible.

The processes of donning and glove flexing during use involve stretching. Therefore, it is important that the gloves, particularly medical gloves, are stretchable, i.e., have tensile properties good enough to prevent tearing or breakage during donning or use. Any coatings applied to the glove for easy donnability should not interfere with the tensile properties and stretch properties of the rubber elastomer of the glove.

Other important properties of gloves, particularly surgical gloves, include a good comfortable feel during use. To achieve this, the gloves must fit well without bagginess contouring the shape of the hand. The glove is stretched over the hand surface with a nearly uniform stretch everywhere with no particular area being stretched more than other areas, since this highly stretched area will result in a pinching glove feel. This proper glove fit is designed into the glove shape by using a former with the shape of the hand. In addition, the elastomeric materials used for the glove must be soft and stretchable so that the hands experience minimal stress while using them. Unfortunately, soft materials, such as natural rubber and polyisoprene, are normally tacky and, therefore, require a surface treatment, such as chlorination, siliconization, or a polymer coating to circumvent this inherent tackiness. The polymer coating process laminates the surface of the glove with a thin layer of synthetic polymer, normally up to several micrometers in thickness, having a low-friction coefficient value to provide anti-tack and good slip properties, as disclosed in U.S. Pat. No. 6,709,725 to Lai et al., which discloses a natural or synthetic rubber elastomeric article having a coating layer containing a blend of a film-forming polymer and a wax. A powder-free glove article also can be made without chlorination, using a powder-free coagulant system as disclosed in U.S. Pat. No. 6,352,666 to Nile et al., which discloses a process for the manufacture of rubber articles. In this disclosure, a powder-free coagulant for use in latex dipping processes comprises a salt-stable dispersion of a polychloroprene rubber and an inorganic metal salt and a powder-free release agent comprising a polypropylene wax emulsion and a cationic surfactant.

In addition, the cuff of the glove should not slip or roll down during use. If this happens, the user's hand becomes exposed and the chemicals or biological fluids can contaminate the user.

Apart from these properties, it is also essential for the glove or its surfaces to be hand-friendly to the user, especially medical gloves, where the glove is worn for a period of 1-2 hours. Since the glove is a barrier, the skin-generated moisture is trapped between the user's skin and the latex barrier layer of the glove. The latex barrier layer of the glove should contain little or no skin irritants, such as sodium dodecyl sulphate, a commonly used surfactant, or calcium nitrate, a commonly used coagulant, or allergens, such as rubber accelerators and latex proteins, which are other rubber-processing chemicals that can cause skin irritation and allergenic reactions. It is known that healthcare workers commonly wash their hands very often to maintain their hand hygiene. This causes the removal of the protective layer of lipids from the skin and, therefore, the natural skin moisturizer is lost. When the glove is removed, the skin-generated moisture dries rapidly, and the hands quickly become very dry. After prolonged use of a glove, the skin becomes over-dry and cracks can occur. The formation of cracks allows microorganisms, allergens and other harmful substances to enter the body, resulting in skin problems and overall health problems. To address this issue, it has been suggested to apply a moisturizer and other skin-protecting or skin-repair agents to the inner surface of the glove during the glove manufacturing process. However, the application of the moisturizer can have adverse effects on the properties of the glove, including deterioration of the tensile strength of the rubber barrier layer, the wet-look of the inside of a glove, or the blocking of the glove inner surfaces, wherein the inside surfaces of the glove stick to each other, causing difficulty in donning the glove.

U.S. Pat. No. 5,614,202 to DeFina discloses a multi-layer moisturizing glove. The middle layer of the glove is saturated with lotion, which can migrate to the user's hand through the pores of the inner layer, while the exterior layer is made of non-porous material. However, there is no formulation given in the patent.

U.S. Pat. No. 6,638,587 to Wang et al. discloses an elastomeric article having a silicone-based composite coating. An elastomeric article, such as a latex glove, is coated with an aqueous dispersion containing a composite of a silicone-modified polymer, e.g., a silicone-modified polyurethane, and silicone resin particles integrated therein. The interaction between the silicone groups on both the polymer and particles enhances the effectiveness of binding of the particles to the latex material. Gloves and other articles contain a micro-roughened skin-contacting surface and exhibit a reduced coefficient of friction and increased lubricity, thereby enhancing the donning properties. There is no indication that the coating protects skin moisture.

U.S. Pat. No. 6,787,490 to Shipp discloses a glove donning delivery system. A cellulosic substrate includes a flexible, substantially planar sheet of at least one layer. The layer has a front side and a backside with a donning agent associated with at least one side of the sheet. The donning agent is transferable from the sheet to an object or individual apart from the sheet. The donning agent is a biocompatible and sterilizable composition and contains a wetting agent, a silicone, skin health agents, residual antimicrobial substrate agents, antimicrobial agents or aloe vera, vitamin E and emollients. The coating is applied to a cellulosic material, not to a rubber elastomeric product.

U.S. Pat. App. Pub. No. 2004/0115250 to Loo et al. discloses a chamomile/aloe vera treated glove. The treating solution comprises water, glycerol, and a botanical extract for applying to the inner surface of a glove. However, there are no lubricants and surfactants in the formulation.

U.S. Pat. App. Pub. No. 2004/0115379 to Conley et al. discloses a method of treating an elastomeric article. This method includes providing a flexible non-woven fabric substrate having a treatment comprising a behenetrimonium methosulfate, distearyldimonium chloride, and dimethyl dioctadecyl ammonium chloride surfactant. The elastomeric article has an exposed surface, which is the external surface of the elastomeric article. When the elastomeric article is placed with the substrate into a tumbling apparatus, and tumbled at a temperature between 20-80° C., the treatment is transferred from the substrate to the exposed surface of the elastomeric article. The elastomeric article is then inverted and the interior surface is exposed and is tumbled with a silicone lubricant. The surfactant coating on the exterior surface of the elastomeric article is only a surfactant and may improve double donning of a glove. The silicone coating is oily and spreads poorly on the glove inner surface and at best enables easy donning of a glove. It does not help moisture retention and has a clammy glove feel.

U.S. Pat. App. Pub. No. 2004/0217506 to Vistins discloses a method of treating a partially solidified elastomeric matrix. This method provides a transfer substrate of open cell or non-woven material that includes a treatment. The treatment comprises an emollient, a humectant, a skin conditioner, an extract and silicone lubricant or skin health agents. The elastomeric matrix has an exposed surface and contacting the matrix with the transfer substrate transfers the treatment from the substrate to the exposed surface of the elastomeric matrix. Transferring these treatment agents to the exposed surface of a partially solidified elastomeric matrix does not guarantee that any of the treatment agents survive the glove manufacturing process, which includes heating, several stages of washing, and chlorination or other chemical treatments. Besides, the very action of contacting a partially solidified elastomeric matrix on a former and peeling of the substrate may produce holes and other defects on the elastomeric matrix, which is unacceptable in a glove, which is relied on as a barrier layer.

Int'l Pat. App. Pub. No. WO 2004/037305 A1 and U.S. Pat. App. Pub. No. 2004/0126604 to Wang et al. disclose a coating composition for the skin-contacting surface of an elastomeric article. The therapeutic, moisturizing coating composition is thermally stable, withstanding 70° C., and subsequently hydrates when contacted with a moisturized skin surface to convert into a liquid "lotion" form during wearing of the article. Therefore, the coating is not inherently 'moisturizing' but requires skin perspiration to activate the coating. The moisturizer composition consists of a polyhydric alcohol moisturizer, which is pantothenol, glycerin or sorbitol, and an alphahydroxy lactone, which is gluconolactone, which is water soluble and hydratable upon contact with skin. The composition further comprises a water-soluble, film-forming polymer, which is chitosan. For damp-hand or wet-hand donning properties, 1% cetyl pyridinium chloride (CPC) is added to the mixture. There are no water-insoluble emollients in this composition.

U.S. Pat. App. Pub. No. 2004/0241201, which is a continuation of U.S. Pat. App. Pub. No. 2004/0126604, discloses a coating composition containing a hydration promoter and a water-soluble moisturizer, or a water-soluble moisturizer and a water-soluble film forming polymer, or a water-soluble moisturizer and an exfoliant, or a water-soluble moisturizer and microporous particles. However, there are no lubricants to facilitate donning and occlusive moisturizer to promote spreading of the coating in the formulation.

Int'l Pat. App. Pub. No. WO 2004/060338 to Lew et al. discloses a topical skin-care formulation (TSF) and dipped elastomeric rubber polymer articles produced using the TSF. The TSF includes effective amounts of Vitamins A, B and E, alpha-lipoic acid, eucalyptus, jojoba and a carrier, such as an emollient cream, and protects and soothes the human's skin, which is in contact with the surface of the dipped elastomeric rubber polymer article. This oil-based formulation may be applied to a dipped elastomeric article after the final washing step and dried to evaporate water to form a substantially uniform coating. This coating is for dipped elastomeric rubber polymeric articles, such as rubber gloves and condoms, and has the ability to provide the user with the benefits of added protection, due to the coating materials, such as moisturizing, protective and antiseptic properties, and also improved comfort, due to soothing and cooling effects. Non-sterile dipped elastomeric rubber polymeric articles coated with TSF have been shown to have lower bacterial counts than similar uncoated dipped elastomeric rubber polymeric articles. The coating material is claimed not to impair the physical properties of the dipped elastomeric rubber polymeric articles. The composition contains 10-50% emollient cream, which is a carrier, for applying onto the surface of gloves. The drawback of the proposed formulation is that it contains too high a level of emollient, which is normally an oil. Soaking natural rubber and polyisoprene gloves in the high oil content mixture could cause swelling and deterioration in the physical properties of the gloves.

Int'l Pat. App. Pub. No. WO2004/060432 and U.S. Pat. App. Pub. No. U.S. 2004/0122382 to Johnson et al. disclose elastomeric articles with a beneficial coating on the surface. The coating separates from the glove surface and transfers to the skin and emulsifies due to skin-generated moisture. The coating includes a carrier, which is a self-emulsifying wax, and a quaternary ammonium compound behenetrimonium methosulfate. The coating also includes an additive selected from the group consisting of an emollient, a humectant, an antioxidant, a neutralizing agent, a chelating agent, an anti-irritant, a vitamin, a skin conditioner, an alpha-hydroxy acid, a moisturizer, a beneficial botanical agent, and an extract. In addition, the carrier may contain dimethicone silicone polymer. However, this silicone polymer is insoluble in moisture, defeating the self-emulsification of the carrier. This coating relies on the skin-generated moisture to separate the carrier and disperse the beneficial agent on the skin as the carrier emulsifies. There are no active lubricants or surfactants in this composition and, as a result, the distribution of the coating on the skin surface is poor.

Patent Application JP2004/190164 to Ochi et al. discloses novel gloves having the effect of positively moisturizing the skin of the wearer's hand as well as only protecting the hand from stimulation from outside, or reducing stimulation from the glove itself. The glove is formed of rubber or resin, and retains urea at least on the inner surface thereof. The urea is preferably contained in the glove itself, and it is more preferable that the content of the urea is 0.1-10 wt. %. However, the formulation contains no occlusive moisturizer or surfactant for promoting spreading of the coating and a lubricant for facilitating donning of the glove.

Int'l Pat. App. Pub. No. WO2005/036996 and U.S. Pat. App. Pub. No. 2005/0081278 to Williams disclose a polymeric glove with a lotion coating and a method of making same. This disposable glove comprises a polymeric material having an inside surface for contacting the skin of a wearer coated with a film-forming polyurethane compound and an oil-based emollient comprising petrolatum, cetearyl alcohol, cetyl alcohol, C12-15 alkyl Benzoate, cyclomethicone or Ceteareth 20. A method of making the glove is also disclosed. These petroleum and oil-based emollients do not disperse easily in an aqueous coating and cause natural and synthetic rubber articles to swell and, therefore, result in the degradation of tensile strength and elongation properties. In addition, there is no water-soluble moisturizer in the formulation. Furthermore, the use of film-forming polyurethane in the formulation will make it difficult to apply the coating by the off-line tumbling and drying method. This is because the polyurethane, when dried, will stick to the dryer, and this will make subsequent dryer cleaning difficult.

There remains a need in the art for a hand-friendly coating, which coats the hand-contacting surfaces of gloves and facilitates dry donning, wet donning and double donning, while still providing adequate glove-grip properties so that surgical implements can be effectively handled. The coating composition desirably prevents rapid drying of skin-generated moisture when the glove is removed and prevents cracking of skin, thereby providing a protective hand-friendly coating layer. The coating composition desirably does not damage the rubber elastomeric article and compromise its tensile and stretch properties. It is an object of the present invention to provide such a coating as well as a glove comprising such a coating and methods of making such a composition and glove. These and other objects and advantages of the present invention, as well as additional inventive features, will become apparent from the detailed description provided herein.

BRIEF SUMMARY OF THE INVENTION

The present invention provides a hand-friendly rubber glove article having a cuff region and an internal glove region. The glove comprises a dried coating of an emulsified hand-friendly mixture, which comprises at least one water-soluble humectant moisturizer, at least one water-insoluble occlusive moisturizer, at least one water-soluble lubricant, and at least one water-soluble surfactant. The water-insoluble occlusive moisturizer is finely and substantially uniformly dispersed within the mixture. The dried coating retains the water-insoluble occlusive moisturizer and the hand-friendly coating is transferred to the skin of a wearer upon activation with skin-generated moisture. The glove article optionally comprises a fabric-adherent cuff region ranging in width from about 0.5 cm to about 10 cm and/or an internal glove region comprising an integral texturized surface having a surface roughness from about 10 m to about 500 nm.

The present invention further provides a method of producing an emulsified hand-friendly mixture. The method comprises:

a. dissolving in water one or more water-soluble humectant moisturizers, one or more water-soluble lubricants, one or more water-soluble surfactants, and, optionally, one or more water-soluble anti-microbial agents;

b. adding to the resulting solution one or more water-insoluble occlusive moisturizers and, optionally, one or more water-insoluble anti-microbial agents; and c. passing the mixture through a colloidal mill to disperse finely the one or more water-insoluble occlusive moisturizers, whereupon an emulsified hand-friendly mixture is produced.

Still further provided is a method of producing a hand-friendly rubber glove article comprising a cuff region and an integral glove region. The method comprises:

a. dipping a pre-heated former into an aqueous coagulant comprising an inorganic metal salt, calcium carbonate powder, a surfactant, and a thickener, and drying it on the former;

b. dipping the former into rubber latex to form a gelled rubber layer;

c. leaching the glove on the former in hot water;

d. dipping the glove on the former into an aqueous dispersion containing polyurethane, a wax dispersion, and a hardness modifier to form a smooth polymer lining;

e. leaching the glove on the former in hot water;

f. heating and curing the rubber glove on the former;

g. leaching the rubber glove on the former in hot water;

h. drying and stripping the rubber glove from the former;

i. rinsing the glove with water to remove calcium carbonate powder;

j. treating the glove with chlorine water;

k. rinsing the glove with water;

l. tumbling the glove with an emulsified hand-friendly mixture comprising at least one water-soluble moisturizer, at least one water-insoluble occlusive moisturizer, at least one lubricant, and at least one surfactant;

m. pre-drying the glove in a tumble-dryer;

n. spraying the glove with water in the tumble dryer without heating; and o. heating the glove to complete dryness.

BRIEF DESCRIPTION OF THE DRAWING

The FIGURE shows a glove 20 that includes an exterior surface 24 and an interior surface 26.

DETAILED DESCRIPTION OF THE INVENTION

The present invention provides a hand-friendly rubber glove article having a cuff region and an integral glove region. By "hand-friendly" is meant non-irritating, non-allergenic, non-abrasive, non-corrosive, and bio compatible with skin, mucous membranes, and blood. The gloves can be industrial or medical gloves. The medical gloves can be examination gloves or surgical gloves. The glove comprises a dried coating of an emulsified hand-friendly mixture, which comprises at least one water-soluble humectant moisturizer, at least one water-insoluble occlusive moisturizer, at least one water-soluble lubricant, and at least one water-soluble surfactant. The constituents of the hand-friendly mixture can be dissolved, or homogeneously dispersed, suspended, or emulsified in the aqueous medium. The water-insoluble occlusive moisturizer is finely and substantially uniformly dispersed within the mixture. The dried coating retains the water-insoluble occlusive moisturizer maintaining the uniform dispersion, and the hand-friendly coating is transferred to the skin of a wearer upon activation with skin-generated moisture. The glove article optionally further comprises a fabric-adherent cuff region ranging in width from about 0.5 cm to about 10 cm and/or an integral glove region comprising an integral texturized surface having a surface roughness from about 10 nm to about 500 nm as measured by atomic force microscopy. The hand-friendly mixture is emulsified in a colloidal mill producing emulsified particles in a size range of about 0.05 micron (μm) to about 5 micron (μm).

The water-soluble humectant moisturizer can be any soluble humectant moisturizer. The humectant moisturizer penetrates into the skin corneum and attracts and helps retain water. Examples include, but are not limited to, glycerol, lactic acid, a derivative of lactic acid, urea, and a combination of two or more of the foregoing. Preferably, the water-soluble humectant moisturizer is glycerol (e.g., glycerine USP 99.5% (Behn Meyer, UEP Industrial Park, Subang Jaya, Selangor, Malaysia)). Glycerol is preferably present in an amount ranging from about 0.5% to about 10% by weight, more preferably about 3% to about 7% by weight, of the hand-friendly mixture. Alternatively, the water-soluble humectant moisturizer is sodium lactate (Purac Co., Suite 18, Level 22, Tower 2, MNI Twins 11 Jalan Pinang 504 50 Kuala Lumpur Malaysia), potassium lactate, zinc lactate, calcium lactate, magnesium lactate, ammonium lactate, or lactic acid, any one or more of which is preferably present in a total amount ranging from about 0.5% and about 5% by weight of the hand-friendly mixture. Alternatively, the water-soluble humectant moisturizer is urea (Behn Meyer UEP Industrial Park, Subang Jaya, Selangor, Malaysia), which is preferably present in an amount ranging from about 0.5% to about 10% by weight of the hand-friendly mixture.

The water-insoluble occlusive moisturizer can be any suitable occlusive moisturizer. The occlusive moisturizer forms a protective barrier and prevents skin from drying out. It also improves glove donning and double gloving. The water-insoluble occlusive moisturizer should not degrade natural or synthetic rubber by swelling and should not adversely affect tensile and stretch properties of natural or synthetic latex. Examples include, but are not limited to, polydimethylsiloxane (dimethicone), oleyl erucate, and a combination thereof. Preferably, the water-insoluble occlusive moisturizer is polydimethylsiloxane (e.g., DC2-1352, DC-HMW2220, and DC2-1029 (Dow Corning Co., Midland, Mich.). Polydimethylsiloxane is preferably present in an amount ranging from about 0.3% to about 2.0% by weight of the hand-friendly mixture. Alternatively, the water-insoluble occlusive moisturizer is oleyl erucate (e.g., Cetiol J-600 (Cognis Co. 5051 Estecreek Drive, Cincinnati, Ohio)), which is preferably present in an amount ranging from about 0.5% to about 10% by weight of the hand-friendly mixture.

The lubricant can be any suitable lubricant. The lubricant provides smoothness, softness, and moisture, and improves dry-donning and double-gloving. Examples include, but are not limited to, polyethylene oxide, a copolymer of polyethylene glycol and polypropylene glycol, and a combination thereof. Preferably, the lubricant is polyethylene oxide (e.g., Polyox WSR N60K (Amerchol Co., Edison, N.J.)), which is preferably present in an amount ranging from about 0.01% to about 3% by weight of the hand-friendly mixture. Alternatively, the lubricant is a copolymer of polyethylene glycol and polypropylene glycol (e.g., Ucon 75H450 (Dow)), which is preferably present in an amount ranging from about 0.5% to about 10% by weight of the hand-friendly mixture.

The water-soluble surfactant can be any suitable surfactant. The surfactant stabilizes the emulsion of the hand-friendly mixture such that the water-insoluble occlusive moisturizers are well dispersed. The surfactant also improves donning and double-gloving. Examples include, but are not limited to, polyoxyethylene 20 (sorbitan mono-oleate) (e.g., Ecoteric T80 (Huntsman, 500 Huntsman Way, Salt Lake City, Utah), nonyl phenol ethoxylate, and a combination thereof. Preferably, the surfactant is nonyl phenol ethoxylate (e.g., Teric N100 (Huntsman 500 Huntsman Way, Salt Lake City, Utah)). Nonyl phenol ethoxylate is preferably present in an amount ranging from about 0.5% to about 10% by weight of the hand-friendly mixture. Alternatively, the surfactant is polyoxyethylene 20 (sorbitan mono-oleate), which preferably is present in an amount ranging from about 0.5% to about 10% by weight of the hand-friendly mixture.

The hand-friendly coating mixture can additionally comprise an anti-microbial agent. Any suitable anti-microbial agent can be used, as long as it is soluble or dispersible in a water-based emulsion. Examples of suitable anti-microbial agents include, but are not limited to, chlorohexidine or a salt thereof, biguanides or a salt thereof, a chlorinated phenol, nitrophenyl acetate, phenyl hydrazine, polybrominated salicylanilide, 2,4,4'-trichloro-2'-hydroxydiphenyl ether, and chlorohexidine digluconate. Since the process of producing the hand-friendly coating mixture involves colloidal milling, both water-soluble and water-insoluble anti-microbial agents can be incorporated into the hand-friendly coating. Preferably, the anti-microbial agent is present in an amount up to about 5% of the weight of the hand-friendly mixture.

In view of the above, the hand-friendly coating mixture preferably has a surface tension in the range of about 0.01 to about 0.10 N/m. In addition, the hand-friendly coating mixture preferably has a contact angle with the surface ranging from about 5 to about 70 degrees. Hand-friendly coating is used to refer to the hand-friendly mixture after it has been applied to the glove and dried.

The rubber can be a natural rubber, such as a Guayule natural rubber or Hevea natural rubber, or a synthetic rubber, such as a synthetic polyisoprene rubber, polychloroprene, a copolymer of chloroprene and dichlorobutadiene, nitrile butadiene rubber, or a blend of synthetic polyisoprene and nitrile butadiene rubber. Other examples include neoprene latex, polyurethane latex or solution, styrene-isoprene-styrene copolymer solution, or blends thereof.

The present invention further provides a method of producing an emulsified hand-friendly mixture. The method comprises:

a. dissolving in water one or more water-soluble humectant moisturizers, one or more water-soluble lubricants, one or more water-soluble surfactants, and, optionally, one or more water-soluble anti-microbial agents;

b. adding to the resulting solution one or more water-insoluble occlusive moisturizers and, optionally, one or more water-soluble anti-microbial agents; and c. passing the mixture through a colloidal mill to disperse finely the one or more water-insoluble occlusive moisturizers, whereupon an emulsified hand-friendly mixture is produced. The mixture is emulsified by high velocity shearing in a colloid mill such as a Silverson mixer (Silverson Machines, 355 Chestnut St. East Longmeadow, Mass.) running at 10,000 rpm, a Charlotte mill (Chemi Colloid Laboratories, Inc., 55 Herricks Road, Garden City Park, N.Y.), or a Waukesha mill (Waukesha Cherry-Burrell, 611 Sugar Creek Rd. Delavan, Wis.). In the conventional mill, the rotor and stator are adjusted to a clearance of about 0.020 to about 0.080 inches with the mid-range being more advantageous. The one or more water-soluble occlusive moisturizers and, when present, the one or more water-insoluble anti-microbial agents are dispersed to an average particle size of about 0.05 micron (μm) to about 5 micron (μm) in diameter.

Still further provided is a method of producing a hand-friendly rubber glove article comprising a cuff region and an integral glove region. The method comprises:

a. dipping a pre-heated former into an aqueous coagulant comprising an inorganic metal salt, calcium carbonate powder, a surfactant, and a thickener, and drying it on the former;
b. dipping the former into rubber latex to form a gelled rubber layer;
c. leaching the glove on the former in hot water;
d. dipping the glove on the former into an aqueous dispersion containing polyurethane, a wax dispersion, and a hardness modifier to form a smooth polymer lining;
e. leaching the glove on the former in hot water;
f. heating and curing the rubber glove on the former;
g. leaching the rubber glove on the former in hot water;
h. drying and stripping the rubber glove from the former;
i. rinsing the glove with water to remove calcium carbonate powder;
j. treating the glove with chlorine water;
k. rinsing the glove with water;
l. tumbling the glove with an emulsified hand-friendly mixture comprising at least one water-soluble moisturizer, at least one water-insoluble occlusive moisturizer, at least one lubricant, and at least one surfactant;
m. pre-drying the glove in a tumble-dryer;
n. spraying the glove with water in the tumble dryer without heating; and
o. heating the glove to complete dryness.

Preferably, in "d" the glove is dipped to a depth ranging from about 0.5 cm to about 10 cm from the edge of the cuff region of the glove such that the cuff region is fabric-adherent. The method can further comprise packaging the glove in pairs or bulk. If desired, the method can still further comprise sterilizing the packaged gloves by exposing the packaged gloves to gamma radiation. This process is described in copending U.S. Pub. No. 2006/0059604, entitled "Latex Glove With Fabric-Adherent Cuff Region," filed Dec. 1, 2005, which is hereby incorporated by reference in its entirety.

The glove is coated with the emulsified hand-friendly mixture after the latex glove product is cured and rinsed with water for the last time. The hand-friendly mixture disperses uniformly on the interior and exterior surface of the glove, due to the spreading effect imparted by the surfactant present within the hand-friendly mixture. When the hand-friendly mixture is dried, the water in the hand-friendly mixture evaporates, leaving behind a very fine and substantially uniform dispersion of the water-insoluble occlusive moisturizers in a water-soluble coating, even when the coating is very thin. The water-soluble portion of the coating comprises one or more water-soluble humectants, one or more water-soluble lubricants and one or more water-soluble surfactants and, optionally, water-soluble and/or water-insoluble anti-microbial agents as described above. In a final step, the external surface of the glove is washed with a spray of water or the glove is donned on a holder and subjected to water rinsing or spray onto the outer surface to remove the coating on the non skin-contacting surface of the glove, while shielding the inner surface of the glove, which is coated with the hand-friendly mixture, from water rinsing or spray, followed by glove drying. The water-insoluble occlusive moisturizer dispersed within the hand-friendly mixture does not degrade the tensile and stretch properties of natural and synthetic rubber elastomers at the concentrations used in the hand-friendly mixture. Moreover, the quantity of the finely and substantially uniformly dispersed water-insoluble occlusive moisturizer is small compared to the overall volume of the hand-friendly mixture, thereby limiting the amount of exposure of the water-insoluble occlusive moisturizer to the latex elastomeric surface. As a result, the prolonged contact between the hand-friendly coating and the rubber glove surface during glove storage and transportation does not deteriorate the mechanical properties, more particularly, the tensile water-soluble strength and stretch properties of the rubber.

When the user wears the glove, the hand-friendly coating on the skin-contacting surface facilitates the dry donning of the glove due to the presence of a lubricant. Moreover, the water-soluble humectant generally retains a small amount of moisture that also assists the dry donning characteristics and, together with the water-soluble surfactant, disperses the coating on the skin, thereby providing a smooth comfortable feel. The hand-friendly coating is very quickly hydrated by skin-generated moisture and the solubilized water-soluble portion of the hand-friendly coating containing the fine and substantially uniform dispersion of the water-insoluble occlusive moisturizer is effectively distributed on the skin surface of the user, assisted by the presence of a water-soluble surfactant within the dried hand-friendly coating. When the glove is removed after use, the moisture loss and cracking of the skin is prevented by the presence of the fine and substantially uniform dispersion of the water-insoluble occlusive moisturizer, which is delivered to the skin surface by the hand-friendly coating and which prevents rapid evaporation of the skin-generated moisture. In doing so, the water-insoluble occlusive moisturizer acts as a barrier to infection of cracks in the skin with micro-organisms and prevents allergic reactions to offensive proteins in the natural rubber and/or residual chemicals used during manufacture.

The hand-friendly coating is inherently non-tacky and non-blocking when properly applied. Therefore, no prior chlorination may be necessary, avoiding an environmentally unfriendly step. The glove with the hand-friendly coating has a lighter color and provides a softer feel to the user as compared to gloves without the hand-friendly coating. In addition, the dry-hand donning, damp-hand or wet hand donning and double gloving properties of the glove with a hand-friendly coating are also much better. The user also will experience less hand fatigue during use. After removing the glove from the user's hand, the migration of the hand-friendly coating from the glove to the hand by hydration and rubbing action results in skin moisturization, and a smooth, soft, and soothing feel to the user.

The hand-friendly glove article can comprise a fabric-adherent cuff region, which can range in width from about 0.5 cm to about 10 cm. The fabric-adherent cuff prevents the glove from slipping or rolling down during use, while the hand-friendly coating on the inner or skin-contacting surface moisturizes the skin of the user. The method for producing a fabric-adherent cuff comprises the steps of forming a dipped latex article in the usual manner and dipping the portion of the glove that is not required to be tacky in an aqueous dispersion of a film-forming polymer, such as polyurethane or a synthetic wax. The portion of the glove that is not dipped in this aqueous dispersion retains the natural stickiness of the latex product and provides cuff roll down resistance. More specifically, the method comprises dipping a preheated glove former into an aqueous coagulant containing water, an inorganic metal salt, at least one surfactant, a thickener, and calcium carbonate; withdrawing and drying; dipping the glove former into natural rubber, synthetic latexes, or mixtures thereof pre-compounded with substances selected from peroxide, sulfur, an accelerator, an activator, an anti-oxidant, and fillers to form a gelled rubber layer; dipping the glove on the former into an aqueous dispersion containing a film-forming polymer or copolymer, a synthetic wax and a hardness modifier to a level of about 0.5 cm to about 10 cm from the edge of the cuff to produce a fabric-adherent cuff region ranging in width from about 0.5 cm to about 10 cm; leaching the rubber glove on the former in hot water; heating the rubber glove to effect curing and drying; leaching the rubber glove on the former in hot water; withdrawing and drying; stripping the glove from the former; rinsing the glove with water to remove calcium carbonate; chlorinating the glove by tumbling in chlorine water; rinsing the glove with water; optionally neutralizing with soda ash; soaking the glove in the hand-friendly mixture comprising at least one water-soluble humectant moisturizer, at least one water-insoluble occlusive moisturizer, at least one water-soluble surfactant, and at least one water-soluble lubricant as described above; pre-drying the glove in a tumble-dryer; spraying the glove with water to remove the hand-friendly mixture on the outer surface of the glove or optionally donning the glove on a holder and spraying or rinsing the glove with water to remove the hand-friendly mixture from the outer surface of the glove; drying the glove in the tumble-dryer to complete dryness and, optionally, packing the glove in pairs or bulk and, optionally sterilizing the packed gloves.

The hand-friendly glove article can comprise an integral glove region with a textured surface, which can range from about 10 nm to about 500 nm. The hand-friendly mixture accesses the valleys of the textured surfaces such that the valleys act as reservoirs for the hand-friendly mixture. The asperities of the rough surface limit contact between the adjacent surfaces of the interior of the glove, thereby preventing blocking of the glove. The asperities also reduce friction as a glove is donned, providing superior dry- and wet-donning characteristics as well as double-gloving characteristics.

One method of generating a textured surface is by dipping the glove on the former into an aqueous dispersion containing a film-forming polymer or copolymer such as polyurethane or acrylic polymers and copolymers; a synthetic wax such as high density polyethylene wax or oxidized polyethylene wax; and a hardness modifier such as melamine formaldehyde resin, poly(2-hydroxylethyl methacrylate), as disclosed in U.S. Pat. No. 6,709,725 to Lai et al., which discloses an elastomeric article having a layer of natural or synthetic rubber and at least one layer of a coating containing a blend of a film-forming polymer and a wax.

According to the present invention, the efficiency of applying the hand-friendly mixture onto the glove's surface depends on several factors. These include the surface tension of the hand-friendly mixture, which is governed by the hydrophilic and hydrophobic ratio of the components, and the inner surface roughness of the glove. The water-soluble components are hydrophilic, while the water-insoluble components are hydrophobic.

When the surface tension of the hand-friendly mixture is too high, i.e., when the hydrophobic component is too high, the wetting of the glove surface by the mixture is poor and, therefore, less of the hand-friendly mixture is coated onto the glove surface. When a hand-friendly mixture with too high of a surface tension contacts a glove surface, the contact angle is close to 180 degrees, leading to thick, unconnected droplets and a sparse coating. A glove with a coating containing a high hydrophobic component gives an oily clammy feel to the user. On the other hand, when the surface tension of the hand-friendly mixture is too low, i.e., when the hydrophilic component is too high, the wetting of the glove surface by the mixture is too good and, therefore, more hand-friendly mixture is coated onto the surface. This low surface tension results in a contact angle in the range of 0 to 50 degrees and results in a thin coating of the hand-friendly coating mixture. In addition, a glove with a coating containing too high of a hydrophilic component will tend to block, i.e., the inner surfaces will stick to each other. In addition, it will also give a sticky feel to the user, and the glove is not easily donned. The preferred surface tension of the hand-friendly mixture of the subject invention is in the range of about 0.01 to about 0.08 N/m. The preferred contact angle of the hand friendly mixture with the latex surface is about 5 to about 70 degrees.

When the inner surface of the glove is texturized, a larger amount of hand-friendly mixture can be applied without having an oily feel to the hand-friendly coating. Also, the inner surfaces of the glove do not block or stick to each other, since the protrusions of a micro-rough surface prevent complete contact between the hand-friendly coatings applied to the two surfaces coming in contact. In addition, a larger amount of hand-friendly coating is available as a reservoir in the valleys between the protrusions of the micro-rough surface and is coated onto the skin surface when moistened by skin-generated moisture.

The rubber glove suited for the application of the hand-friendly coating on the skin-contacting inner surface can be made by conventional method using a glove former dipped in a calcium carbonate or other powder coagulant system or a powder free system as disclosed in U.S. Pat. No. 6,075,081, U.S. Pat. No. 6,347,409, and U.S. Pat. No. 6,352,666, and then cured. For a glove produced using a powder-free coagulant system, the hand-friendly mixture is applied to the glove online, i.e., while the glove is still on the former, after the curing step. For a glove produced using a powdered coagulant system, after stripping the glove from the former, the glove is rinsed with water, followed by tumbling with a chlorine solution, optionally neutralizing with soda ash, and rinsing with water. This glove is then tumbled in the hand-friendly mixture that coats both the inner and outer surfaces of the glove with the hand-friendly mixture. The glove with the hand-friendly coating is pre-dried in a tumble-dryer at an elevated temperature, preferably at 50-80° C. for 10-60 min. The hand-friendly coating dries and becomes sticky and is coated on both inner and outer surfaces of the glove. The glove is optionally donned on a holder and the glove outer surface is sprayed or rinsed with water to remove the hand-friendly coating on the outside surface, while the coating on the inner surface, being shielded from water rinsing, remains intact. In an alternate embodiment, the glove is tumbled in a tumble-dryer and water is sprayed on the outer surface of the glove and in this case, the coating on the inner surface is largely shielded from water spray and mostly remains intact. The glove is then dried again in the tumble-dryer preferably at 50-80° C. for 30-120 min. The glove can then be packed and sterilized with gamma irradiation.

EXAMPLES

The following examples, which are summarized in Table 1, further illustrate the present invention and are not intended to limit its scope in any way. The symbol "%" used in the examples refers to "% by weight" unless otherwise specified. The ratings used in the evaluation of the glove in the following examples for donnability, double gloving, blocking, and wet-look of the glove are described in Table 2, while softness, smoothness, and moisturizing feels are described in Table 3.

TABLE 1

Summary of Examples (1) to (4)

| Example | Hand-friendly Coating | Fabric-adherent cuff region | Pre-drying before water spray |
|---|---|---|---|
| Example 1 | Yes | Yes | Yes |
| Example 2 | Yes | Yes | No |
| Example 3 | No | Yes | Yes |
| Example 4 | Yes | No | Yes |

TABLE 2

Ratings on glove donnability, double gloving, blocking, and wet-look of gloves

| Rating | Dry Donnability | Damp-/wet-hand Donnability | Double Gloving | Blocking | Wet-look |
|---|---|---|---|---|---|
| 1 | Very difficult | Very difficult | Very difficult | No blocking | No wet-look |
| 2 | Difficult | Difficult | Difficult | Slight blocking | Slight wet-look |
| 3 | Acceptable | Acceptable | Acceptable | Severe blocking | Severe wet-look |
| 4 | Easy | Easy | Easy | — | — |
| 5 | Very easy | Very easy | Very easy | — | — |

TABLE 3

Ratings on glove softness, hand smoothness and moisturizing feel

| Rating | Softness | Smoothness | Moisturizing feel |
|---|---|---|---|
| 1 | Very stiff | Very sticky | Very poor |
| 2 | Stiff | Sticky | Poor |
| 3 | Acceptable | Acceptable | Acceptable |
| 4 | Soft | Smooth | Good |
| 5 | Very soft | Very smooth | Very good |

TABLE 4

Hand-friendly coating mixture

| Component | Percentage by weight |
|---|---|
| DC2-1352 Silicone Emulsion (water-insoluble occlusive moisturizer) | 1.20% |
| Polyox WSR N60K (lubricant) | 0.50% |
| Glycerol (water-soluble humectant) | 5.00% |
| Sodium lactate (water-soluble humectant) | 1.00% |
| Teric N100 (surfactant) | 2.30% |
| Water | 90.0% |

Example 1

Preparation of a Glove with a Hand-Friendly Coating on the Skin-Contacting Surface and a Fabric-Adherent Cuff Region (with Pre-Drying)

Step 1 A surgical glove former was dipped into an aqueous coagulant containing 20% calcium nitrate, 5% calcium carbonate powder, 0.1% Teric 340 (Huntsman 500 Huntsman Way, Salt Lake City, Utah), and 0.2% cellusize QP30,000 (Union Carbide, Danbury, Conn.), and dried on the former.

Step 2 The glove on the former was dipped into prevulcanized natural rubber latex with 35% total solid content to form a gelled rubber layer.

Step 3 The glove on the former was leached in hot water at 60° C. for 5 min.

Step 4 The glove was dipped into an aqueous dispersion containing 10% Beetafin PU L9009 (BIP (Oldbury) Limited, Tat Bank Road, Oldbury, West Midlands, United Kingdom), 3% Aquamat 213 (BYK-Chemie, Wesel, Germany), and 1% Cymel 373 (Cytec Industries, 1405 Buffalo Street, Olean, N.Y.) up to a level of 3 cm from the cuff edge of latex film to form a thin polymer lining extending from 3 cm below the cuff edge. The portion of the glove not coated by the aqueous dispersion retains the natural tackiness of latex forming the fabric-adherent cuff region.

Step 5 The glove on the former was heated and cured in an oven at 130° C. for 10 mm.

Step 6 The glove on the former was leached in hot water at 80° C. for 30 sec, dried, and stripped from the former.

Step 7 The glove was rinsed with water to remove calcium carbonate powder.

Step 8 The outer surface of the glove was treated with 0.5 g/l chlorine water for 10 sec.

Step 9 The glove was then rinsed with water.

Step 10 The glove was tumbled with a hand-friendly coating mixture as shown in Table 4, prepared by emulsifying the mixture with a Silverson mixer operating at 10,000 rpm for 30 min to obtain an average particle size of 0.3 micron (μm) in diameter or lower. After 30 min of tumbling with the hand-friendly mixture, the mixture was drained.

Step 11 The glove was then pre-dried in a tumble-dryer for 30 min at 70° C.

Step 12 Water was sprayed onto the glove in the tumble-dryer, without heating, for 6 min to remove the hand-friendly coating from the outer surface of the glove.

Step 13 The glove was dried to complete dryness at 70° C. for 80 min.

Step 14 The glove was packed and sterilized with gamma irradiation.

Example 2

Preparation of a Glove with a Hand-Friendly Coating on the Skin-Contacting Surface and a Fabric-Adherent Cuff Region (without Pre-Drying)

All the steps in Example 1 were repeated except step 11.

Example 3

Preparation of a Glove without a Hand-Friendly Coating on the Skin-Contacting Surface but with Fabric-Adherent Cuff Region All the steps in Example 1 were repeated except that steps 10 to 12 were omitted.

Example 4

Preparation of a Glove with a Hand-Friendly Coating on the Skin-Contacting Surface without a Fabric-Adherent Cuff Region (with Pre-Drying)

All the steps in Example 1 were repeated, except that in step 4 the glove was dipped into an aqueous dispersion containing 10% Beetafia PU L9009, 3% Aquamat 213, and 1% Cymel 373 up to the brink of the cuff. The inner surface of the glove was fully coated with a polymer without a fabric-adherent cuff region.

Example 5

Evaluation of Dry-Hand Donning Properties

Five testers donned the gloves from Examples (1) to (3) with their dry hands, and each tester gave his rating according to the ease of donning the glove as shown in Table 2. The results are shown in Table 5.

TABLE 5

| Dry-hand donning properties | |
|---|---|
| Sample | Average Rating |
| Example 1 | 5 |
| Example 2 | 5 |
| Example 3 | 3 |

The results show that application of the hand-friendly coating to the skin-contacting surface of the glove significantly improved the dry-hand donning properties of the glove when compared to a glove without the hand-friendly coating. Without the pre-drying step, the dry-hand donning properties of the glove were not affected.

Example 6

Evaluation of Damp-Hand Donning Properties

Five testers were given the gloves from Examples (1) to (3) to don with their damp-hands, and each tester gave his rating according to the ease of damp-hand donning as categorized in Table 2. The results are shown in Table 6.

TABLE 6

| Damp-hand donning properties | |
|---|---|
| Sample | Average Rating |
| Example 1 | 5 |
| Example 2 | 3 |
| Example 3 | 2 |

The results indicate that the glove with the hand-friendly coating had improved damp-hand donning properties as compared to the glove without the hand-friendly coating. Furthermore, pre-drying helped to improve further the damp-hand donning properties.

Example 7

Evaluation of Double-Gloving Properties

Five testers were given two identical gloves of the same size, one on top of the other, from Examples (1) to (3), and each tester gave his rating according to the ease of double-gloving as categorized in Table 2. The results are shown in Table 7.

TABLE 7

| Double-gloving properties | |
|---|---|
| Sample | Average Rating |
| Example 1 | 5 |
| Example 2 | 4 |
| Example 3 | 2 |

The results indicate that the glove with the hand-friendly coating had improved the double-gloving properties as compared to that without the hand-friendly coating. Furthermore, pre-drying helped to improve further the double-gloving properties of the glove.

Example 8

Evaluation of Cuff Pull Force

To measure cuff roll down resistance, a sleeve of a disposable surgeon's gown was first put on a former having the shape of a human arm. The glove was then put on the arm former with the cuff covering part of the gown sleeve. The glove was then pulled at a constant speed to detach from the gown sleeve. The force required to detach the glove from the gown sleeve was measured as cuff pull force. The gloves from Examples (1) to (4) were tested for this cuff pull force and the results are summarized in Table 8.

TABLE 8

| Cuff pull force | |
|---|---|
| Sample | Force, Kg |
| Example 1 | 4.2 |
| Example 2 | 4.0 |
| Example 3 | 4.4 |
| Example 4 | 1.0 |

Results in Table 8 show that in the presence of a fabric-adherent cuff region, i.e., Examples (1) to (3), the resistance against cuff roll down of the glove, as indicated by the cuff pull force, is higher than that without the fabric-adherent cuff region. In the presence of the hand-friendly coating, the resistance against cuff roll down remained unaffected.

Example 9

Evaluation of Skin Moisturization

An instrument called a corneometer can quantify the skin moisture content of the hand. To evaluate the skin moisturization effects of the glove with the hand-friendly coating, the skin moisture content (SMC) of both hands of 30 subjects was first measured using a Multiple Probe Adapter 5 with CM 825 corneometer probe (manufactured by CK Electronic, Germany) after being conditioned for 30 min in a room with relative humidity of 50±5% and temperature of 22+2° C. The subjects were then given a glove from Example 1 to wear on one hand and a glove from Example 3 on the other hand. After one hour, the gloves were removed from their hands and the skin moisture content was measured again, 5 min after the removal of the gloves, under the same controlled environment described above. The improved skin moisturization after wearing the glove is given by the following equation:

Improved skin moisturization=[(SMC after−SMC before)×100%]÷(SMC before), where "SMC after" and "SMC before" refer to skin moisture content after wearing glove and skin moisture content before wearing glove, respectively.

The results of 30 subjects are summarized in Table 9.

TABLE 9

| | Improved skin moisturization |
|---|---|
| Sample | Average improved skin moisturization |
| Example 1 | 68% |
| Example 3 | 33% |

From the results in Table 9, it is clear that the glove with the hand-friendly coating provided improved skin moisturization than that without the hand-friendly coating.

Example 10

Tensile Properties

The tensile properties of the gloves, both unaged and aged (70° C. for 7 days), were determined using the ASTM D-3577 (ASTM International, 100 Barr Harbor Drive, PO Box C700, West Conshohocken, Pa.) method. The results are summarized in Table 10.

TABLE 10

| | Tensile properties of gloves | | | |
|---|---|---|---|---|
| | ASTM D-3577 | | | |
| | Ultimate tensile strength (MPa) | | Elongation at break (%) | |
| Sample | Unaged | Aged | Unaged | Aged |
| Example 1 | 28 | 24 | 890 | 930 |
| Example 3 | 28 | 24 | 900 | 930 |

The results in Table 10 indicate that the hand-friendly coating does not affect the tensile properties of the glove.

Example 11

Evaluation of Blocking

Gloves from Examples 1 and 3 were aged in oven at 50° C. for 7 days. The extent of blocking was evaluated using the criteria shown in Table 2.

TABLE 11

| | Evaluation of blocking | |
|---|---|---|
| Sample | Glove-to-glove blocking* | Glove-to-pack blocking** |
| Example 1 | 1 | 1 |
| Example 3 | 1 | 1 |

Note:
*The extent the inside surfaces of the glove, where they are in contact with each other, sticking to each other.
**The extent the outer surfaces of the glove, where they are in contact with paper, sticking to that paper.

The results in Table 11 show that the hand-friendly coating does not cause any blocking to the glove.

Example 12

Evaluation of Wet-Look

Gloves from Examples 1 and 3 were visually inspected for wet-look. The extent of wet-look was evaluated using the criteria shown in Table 2.

TABLE 12

| | Evaluation of wet-look |
|---|---|
| Sample | Extent of wet-look |
| Example 1 | 1 |
| Example 3 | 1 |

The results in Table 12 indicate that the hand-friendly coating does not cause wet-look to the glove.

Example 13

Evaluation of Softness of Glove

Five testers in a panel were given a glove from Example 1 to wear on one hand and a glove from Example 3 to wear on the other hand. The softness of the gloves was evaluated by flexing their hands. The average ratings were summarized in Table 13.

TABLE 13

| | Softness of glove |
|---|---|
| Sample | Average rating |
| Example 1 | 5 |
| Example 3 | 3 |

The results in Table 13 indicate that the glove with the hand-friendly coating is softer than that without the hand-friendly coating.

Example 14

Evaluation of Hand Smoothness Feel

Five testers were given a glove from Example 1 to wear on one hand and a glove from Example 3 to wear on the other hand. After wearing for one hour, both gloves were removed from the hands and the smoothness of the hands was evaluated 5 min after the removal of the gloves. The average ratings of the testers were summarized in Table 14.

TABLE 14

| | Hand smoothness feel |
|---|---|
| Sample | Average rating |
| Example 1 | 5 |
| Example 3 | 3 |

The results in Table 14 indicate that the glove with the hand-friendly coating gave a smoother feel to the user's hand than that without the hand-friendly coating after wearing.

Example 15

Evaluation of Hand Moisturizing Feel

Five testers were given a glove from Example 1 to wear on one hand and a glove from Example 3 to wear on the other hand. After wearing for one hour, both gloves were removed from the hands and the moisturizing feel of hands was evaluated 5 min after the removal of the gloves. The average rating of the testers were summarized in Table 15.

TABLE 15

Hand moisturizing feel of hand

| Sample | Average rating |
| --- | --- |
| Example 1 | 5 |
| Example 3 | 2 |

The moisturizing feel of the user's hand after wearing the glove having the hand-friendly coating was found to be much better than that having no hand-friendly coating.

Example 16

Human Skin Irritation Test Based on ISO 10993 (ISO 10993-13:1998, Biological Evaluation of Medical Devices—Part 13: Identification and Quantification of Degradation Products from Polymeric Medical Devices)

The purpose of this test is to determine the potential skin irritation of the glove following acute exposure. A 2 cm×2 cm glove sample was secured onto the skin of 30 test subjects by means of occlusive tape for 48 hours. Upon completion, the patch was removed and the treatment site was examined for up to 48 hours.

The severity of irritation potential was graded as in Table 16.

TABLE 16

Irritation potential classification

| Percentage of irritation to total subject | Classification |
| --- | --- |
| 0-5% | Non-irritant |
| > 5%-10% | Minimal |
| >10%-30% | Mild |
| >30%-50% | Moderate |
| >50%-80% | Severe |
| >80% | Maximum |

The results of the study on the gloves from Example 1 and 3 using 0.5% sodium dodecyl sulfate as a positive control and 0.9% sodium chloride as a negative control are shown in Table 17.

TABLE 17

Irritation potential of gloves

| Sample | Percentage of irritation | Classification |
| --- | --- | --- |
| 0.5% sodium dodecyl sulfate | 66% | Severe |
| 0.9% Sodium chloride | 0% | Non-irritant |
| Example 1 | 0% | Non-irritant |
| Example 3 | 0% | Non-irritant |

Both samples from Examples 1 and 3 were found to be non-irritating, while sodium dodecyl sulfate and sodium chloride were severely irritating and non-irritating, respectively. Therefore, the hand-friendly coating does not cause skin irritation to the glove user.

Example 17

Interaction with Blood Test Based on ISO 10993

The purpose of this test is to determine whether the leachables from the gloves would cause hemolysis in vitro, a measurement of blood compatibility. Blood samples were obtained from three rabbits, pooled, diluted and added to the glove's extracts. Each sample was then gently mixed and maintained at 37° C. for 4 hrs. After the incubation period, the samples were centrifuged and the resulting supernatant was added to Drabkin's reagent (A solution used in the cyanmethemoglobin method of measuring hemoglobin. It consists of sodium bicarbonate, potassium cyanide, and potassium ferricyanide). The percentage of transmission of the extracts was measured with a spectrophotometer at a wavelength of 540 nm. Using this absorbance value, the hemoglobin concentration was calculated from a hemoglobin standard curve. The percent of hemolytic index was calculated using the following equation:

$$\frac{\text{Hemoglobin concentration of sample}}{\text{Hemoglobin present}} \times 100\% = \%\ \text{Hemolytic Index.}$$

The mean hemolytic index was the average value from duplicate samples. A hemolytic grade was assigned based on the following scheme:

TABLE 18

Hemolytic Index and Hemolytic Grade

| Hemolytic Index | Hemolytic Grade |
| --- | --- |
| 0-2% | Non-hemolytic |
| 3%-10% | Slightly hemolytic |
| 11%-20% | Moderately hemolytic |
| 21%-40% | Markedly hemolytic |
| Above 40% | Severely hemolytic |

The results of the study on the gloves from Examples 1 and 3 together with the positive control and negative control are shown in Table 19.

TABLE 19

Hemolytic grade of glove's extracts

| Sample | Hemolytic Index | Hemolytic Grade |
| --- | --- | --- |
| Positive Control | 96.1% | Severely hemolytic |
| Negative Control | 0.0% | Non-hemolytic |
| Example 1 | 0.0% | Non-hemolytic |
| Example 3 | 0.0% | Non-hemolytic |

The results in Table 19 show that the extracts of gloves from both Examples 1 and 3 are compatible with blood, implying that the introduction of the hand-friendly coating to the glove does not change the blood compatibility of the glove's extract.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. It should be understood that the illustrated embodiments are exemplary only, and should not be taken as limiting the scope of the invention.

What is claimed is:

1. A rubber glove comprising a cured latex glove and a dried coating of an emulsified mixture on an interior surface of the glove, the hand friendly mixture consisting essentially of:
    a water-soluble portion containing at least one water-soluble humectant moisturizer selected from the group consisting of glycerol, lactic acid, a derivative of lactic acid, urea, and a combination of two or more of the foregoing, at least one water-soluble lubricant selected from the group consisting of polyethylene oxide, a copolymer of polyethylene glycol and polypropylene glycol, and a combination thereof, at least one water-soluble surfactant, and optionally one or more water-soluble anti-microbial agents, and
    a water-insoluble occlusive moisturizer, selected from the group consisting of polydimethylsiloxane (dimethicone), oleyl erucate, and a combination thereof, that is finely and substantially uniformly dispersed within the water-soluble portion and, optionally, one or more water-insoluble antimicrobial agents, wherein the water-insoluble moisturizer and optional water-insoluble antimicrobial agents are dispersed, wherein the surfactant stabilizes the emulsified mixture such that the water-insoluble occlusive moisturizers are well dispersed,
    wherein the dried coating is on the interior surface of the glove, wherein upon contact of the interior surface with skin-generated moisture of a wearer's skin, the dried coating is transferred to the skin, and
    wherein the elongation at break (%) and the ultimate tensile strength of the glove aged for 7 days at 70° C. is substantially the same as the elongation at break (%) and ultimate tensile strength of a cured latex glove of equivalent manufacture, except lacking the emulsified mixture, aged for 7 days at 70° C.

2. The rubber glove of claim 1, wherein the water-insoluble occlusive moisturizer is substantially uniformly dispersed within the dried coating.

3. The rubber glove of claim 1, wherein the at least one water-soluble humectant moisturizer is glycerol in an amount ranging from about 0.5% to about 10% by weight of the mixture.

4. The rubber glove of claim 1, wherein the water-insoluble occlusive moisturizer is polydimethylsiloxane in an amount ranging from about 0.3% to about 2.0% by weight of the mixture.

5. The rubber glove of claim 1 wherein the water-insoluble occlusive moisturizer is oleyl erucate present in an amount ranging from about 0.5% and 10% by weight of the mixture.

6. The rubber glove of claim 1, wherein the at least one water-soluble lubricant is polyethylene oxide present in an amount ranging from about 0.01% to about 3% by weight of the mixture.

7. The rubber glove of claim 1, wherein the at least one water-soluble surfactant is selected from the group consisting of polyoxyethylene 20 (sorbitan mono-oleate), nonyl phenol ethoxylate, and a combination thereof.

8. The rubber glove of claim 7, wherein the at least one surfactant is nonyl phenol ethoxylate present in an amount ranging from about 0.5% to about 10% by weight of the mixture.

9. The rubber glove of claim 7, wherein the at least one surfactant is polyoxyethylene 20 (sorbitan mono-oleate) present in an amount ranging from about 0.5% to about 10% by weight of the mixture.

10. The rubber glove of claim 1, wherein the mixture additionally comprises a said water-insoluble anti-microbial agent.

11. The rubber glove of claim 1, wherein the mixture includes anti-microbial agent(s) selected from the group consisting of chlorohexidine or a salt thereof, biguanides or a salt thereof, a chlorinated phenol, nitrophenyl acetate, phenyl hydrazine, polybrominated salicylanilide, 2,4,4'-trichloro-2'-hydroxydiphenyl ether, chlorohexidine digluconate, and combinations thereof.

12. The rubber glove of claim 11, wherein the anti-microbial agent(s) are present in an amount up to about 5% of the weight of the mixture.

13. The rubber glove of claim 1, wherein the mixture has a surface tension in the range of about 0.01 to about 0.10 N/m.

14. The rubber glove of claim 1, wherein the mixture has a contact angle with the surface ranging from about 5 to about 70 degrees.

15. The rubber glove of claim 1, wherein the rubber is selected from the group consisting of natural rubber, Guayule natural rubber, Hevea natural rubber, synthetic rubber and synthetic polyisoprene rubber.

16. The rubber glove of claim 15, wherein the synthetic rubber is selected from the group consisting of polychloroprene, dichlorobutadiene, nitrile butadiene rubber and combinations thereof.

17. The rubber glove of claim 1, wherein the internal glove region comprises an internal surface having a surface roughness from about 10 nm to about 500 nm.

18. The rubber glove of claim 1, wherein the amount of blocking of the glove is substantially the same as the amount of blocking of a cured latex glove of equivalent manufacture, except lacking the emulsified mixture.

19. The rubber glove of claim 1, wherein the glove increases skin moisturization of a user compared to a glove of equivalent manufacture except lacking the emulsified mixture.

20. The rubber glove of claim 1, wherein the mixture additionally includes a water-soluble anti-microbial agent.

* * * * *